United States Patent
Muniz et al.

(10) Patent No.: US 10,960,076 B2
(45) Date of Patent: Mar. 30, 2021

(54) GUMMY DOSAGE FORMS COMPRISING SERINE

(71) Applicant: Church & Dwight Co. Inc., Princeton, NJ (US)

(72) Inventors: Luis C. Muniz, Far Hills, NJ (US); Albert Nazareth, Mercerville, NJ (US); Paul A. Cox, Jackson Hole, WY (US); Robert Frank Boutin, Hinsdale, IL (US)

(*) Notice: Subject to any disclaimer, the term of this patent is extended or adjusted under 35 U.S.C. 154(b) by 0 days.

(21) Appl. No.: 15/879,345

(22) Filed: Jan. 24, 2018

(65) Prior Publication Data

US 2018/0207282 A1  Jul. 26, 2018

Related U.S. Application Data

(60) Provisional application No. 62/450,307, filed on Jan. 25, 2017.

(51) Int. Cl.
| | |
|---|---|
| *A61K 47/36* | (2006.01) |
| *A61K 9/06* | (2006.01) |

(Continued)

(52) U.S. Cl.
CPC ............ *A61K 47/36* (2013.01); *A61K 9/0058* (2013.01); *A61K 9/06* (2013.01); *A61K 31/198* (2013.01);

(Continued)

(58) Field of Classification Search
None
See application file for complete search history.

(56) References Cited

U.S. PATENT DOCUMENTS

| | | | |
|---|---|---|---|
| 5,656,608 A * | 8/1997 | Schneider | ............ A61K 31/195 514/42 |
| 6,048,543 A | 4/2000 | Schneider et al. | |

(Continued)

FOREIGN PATENT DOCUMENTS

| | | |
|---|---|---|
| KR | 100432039 | 7/2004 |
| WO | 2012092391 | 7/2012 |
| WO | 2012173587 | 12/2012 |

OTHER PUBLICATIONS

Food & Beverage Online, "Amino Acids Gummy Candy (Vegetarian)", https://www.21food.com/products/amino-acids-gummy-candy-(vegetarian)-759670.html, printed May 31, 2016, 2 pages. CN.

(Continued)

*Primary Examiner* — Aradhana Sasan
(74) *Attorney, Agent, or Firm* — Church & Dwight Co., Inc.

(57) ABSTRACT

The present disclosure describes a gummy dosage form including: an amino acid in an amount of about 20% by weight or greater; a hydrophilic bulking agent; and a hydrophilic long-chain polymer, wherein at least a portion of the hydrophilic long-chain polymer comprises low methoxyl pectin. The gummy dosage forms can further include additives such as flavorants, fiber, and pH-adjusters. The disclosure further comprises methods for preparing such gummy dosage forms, wherein a hydrophilic bulking agent, a hydrophilic long-chain polymer, and water are combined to give a mixture and heated to give a hydrocolloid system in the form of a slurry; mixing an amino acid with the slurry; and setting the resulting mixture to give the gummy dosage form.

19 Claims, 2 Drawing Sheets

(51) Int. Cl.
*A61K 31/198* (2006.01)
*A61P 25/28* (2006.01)
*A61K 47/26* (2006.01)
*A61K 9/68* (2006.01)
*A61P 25/14* (2006.01)
*A61P 25/16* (2006.01)

(52) U.S. Cl.
CPC .............. *A61K 47/26* (2013.01); *A61P 25/14* (2018.01); *A61P 25/16* (2018.01); *A61P 25/28* (2018.01)

(56) References Cited

U.S. PATENT DOCUMENTS

| | | | |
|---|---|---|---|
| 6,310,097 | B1 | 10/2001 | Mitoma et al. |
| 6,458,395 | B1 | 10/2002 | Emoto |
| 6,663,910 | B2 | 12/2003 | Soumya et al. |
| 6,942,886 | B2 | 9/2005 | Katz |
| 7,223,417 | B2 | 5/2007 | Calton et al. |
| 7,378,118 | B2 | 5/2008 | Song et al. |
| 7,537,792 | B2 | 5/2009 | Niekerk et al. |
| 9,232,810 | B2 | 1/2016 | Cao et al. |
| 2005/0226948 | A1 | 10/2005 | Lee et al. |
| 2007/0020370 | A1 | 1/2007 | Schymura |
| 2007/0116820 | A1 | 5/2007 | Prakash et al. |
| 2007/0202058 | A1 | 8/2007 | Calton |
| 2008/0026038 | A1* | 1/2008 | Steele .................. A23G 3/0025 424/440 |
| 2009/0155363 | A1 | 6/2009 | Maibach |
| 2010/0119664 | A1 | 5/2010 | Stawski |
| 2010/0226904 | A1 | 9/2010 | Davis |
| 2010/0330058 | A1 | 12/2010 | Davis |
| 2011/0071119 | A1 | 3/2011 | Davis |
| 2012/0035277 | A1 | 2/2012 | Davis |
| 2013/0052307 | A1 | 2/2013 | Elejalde et al. |
| 2014/0094434 | A1 | 4/2014 | Hirabayashi et al. |
| 2014/0212893 | A1 | 7/2014 | Cox et al. |
| 2015/0216199 | A1* | 8/2015 | Porter ...................... A23G 3/44 426/72 |
| 2016/0296474 | A1 | 10/2016 | Romanoschi et al. |

OTHER PUBLICATIONS

Fuel Your Fitness Method, "Alpha Amino Acid Gummy Bears", http://inspirelinge.blogspot.com/2014/06/alpha-amino-gummybears.html, published Jun. 17, 2014, 1 page. US.

splicd.com, "Amino Acids Gummy Candy (Pectin, Vegan)", http://www.splicd.com/wholesale/pz53bc694-cz5ef41de-amino-acidsgummy-candy-pectin-vegan.html, 2 pages, printed May 31, 2016. CN.

The Crafty Feminist, "DIY Gummy Candy—No Mold Required!", https://thecraftyfeminist.com/2014/08/12/diy-gummy-candy-no-mold/, 7 pages, printed May 31, 2016, US.

* cited by examiner

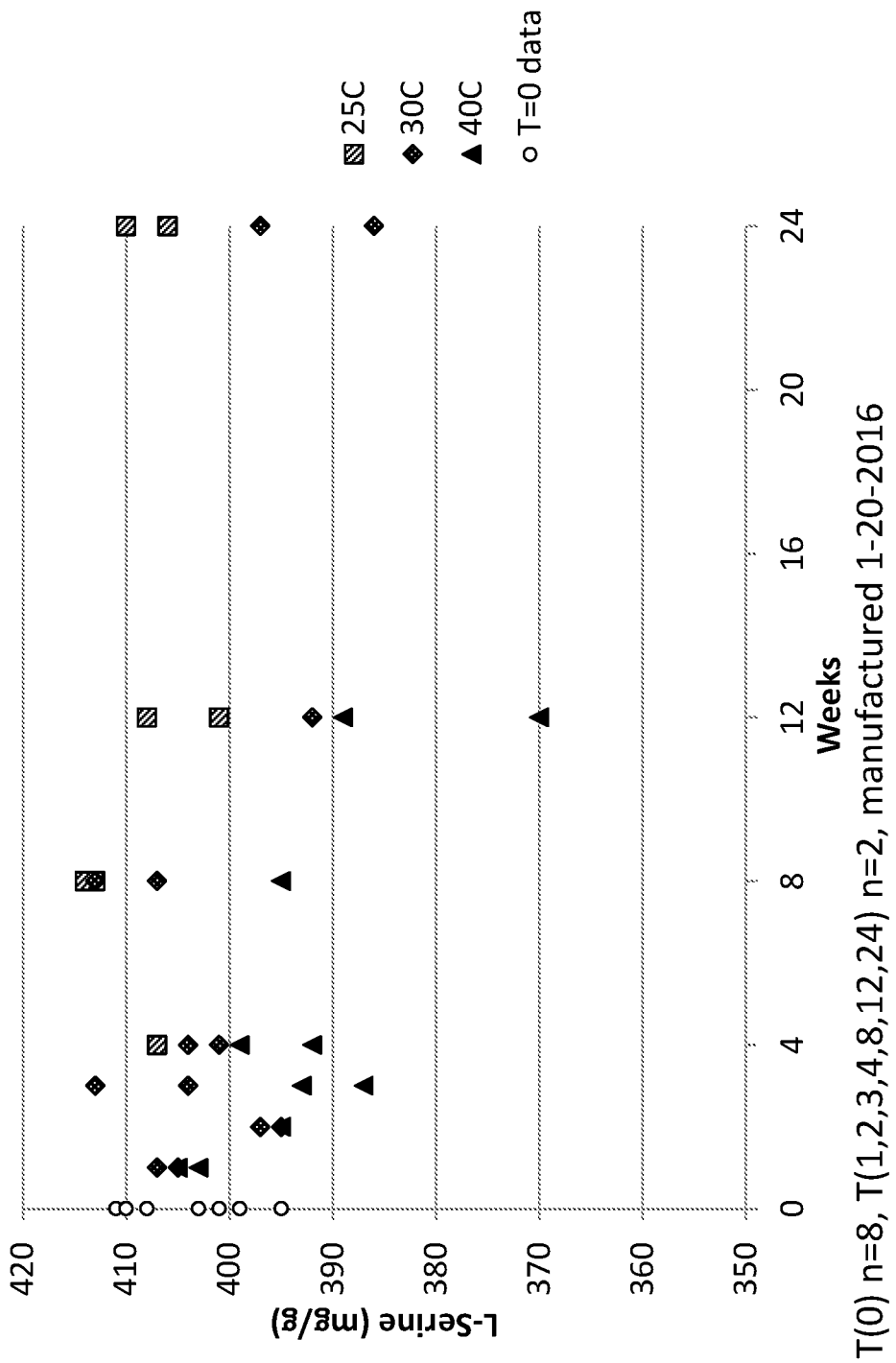

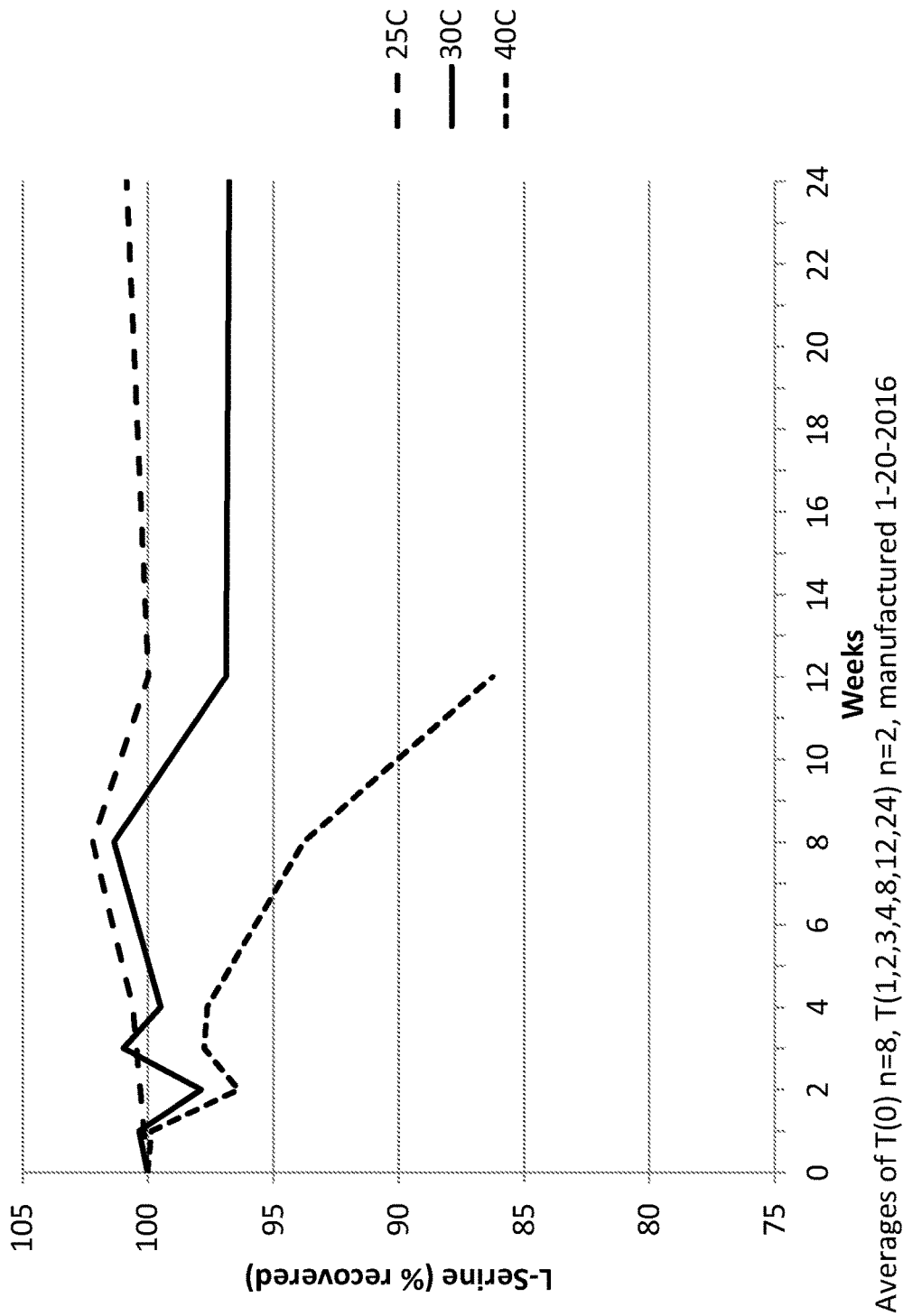

GUMMY DOSAGE FORMS COMPRISING SERINE

CROSS-REFERENCE TO RELATED APPLICATIONS

The present application claims priority to U.S. Provisional Application No. 62/450,307, filed Jan. 25, 2017, which is hereby incorporated in its entirety by reference in this application.

FIELD OF THE DISCLOSURE

The present disclosure relates to orally ingestible dosage forms and methods for making such dosage forms. The dosage forms can contain a higher weight percentage of active pharmaceutical ingredients than conventional dosage forms.

BACKGROUND OF THE INVENTION

Oral dosing of many materials with desirable properties and functions can be problematic when provided in a chewable form because the intrinsic taste of such materials can be unpleasant, particularly in children and geriatric adults. The intrinsic bitterness of certain active pharmaceutical ingredients (APIs) in particular can present a major obstacle to the acceptance, compliance, and effectiveness of treatments including oral, chewable dosing.

Previous approaches to addressing the problem of poor palatability of certain materials have been based mainly on nullifying undesirable tastes using flavor additives, chemical chelation (e.g., using ion exchange resins and β-cyclodextrins) and physical encapsulation. These systems can be adapted into solid dosage forms or liquid-based formulations as solutions, suspensions, or multi-phase emulsions.

Gummy dosage forms are particularly effective for enabling compliant dosing in children, as well as geriatric adults, as these forms provide a palatable, chewable base, can incorporate APIs, and have low intrinsic taste response. However, while gummy dosage forms provide the basis for effective dosing of active ingredients to children (and geriatric patients) their application for the delivery of certain APIs and like materials has been highly restrictive due to the limited number of active ingredients that are compatible with the gummy dosage platform and/or difficulties with incorporating the API in a sufficiently high concentration.

One type of active ingredient that would be desirably incorporated within a gummy form includes amino acids, which are promising candidates for treatment of a wide range of illnesses. For example, L-serine is being studied for the treatment of neurological brain diseases such as Amyotrophic Lateral Sclerosis (ALS), Alzheimer's Disease, and Parkinson's Disease. However, the inclusion of sufficient quantities of amino acids remains a challenge. It would be beneficial to provide methods for providing relatively high quantities of such active ingredients in gummy dosage forms so as to provide gummy dosage forms having relatively high concentrations of these active ingredients.

SUMMARY OF THE DISCLOSURE

The present disclosure provides chewable, gummy dosage forms that are adapted for the delivery of active ingredients such as amino acids to individuals, including those who may have difficulty swallowing conventional oral dosage forms (e.g., children and geriatric adults) and those who have an aversion to the taste of the active ingredients or have dosing fatigue to swallowing pills. The present disclosure provides formulations of active ingredients in relatively high concentrations within such dosage forms.

In one aspect, the disclosure provides a gummy dosage form comprising: one or more hydrophilic bulking agents; one or more hydrating materials; an amino acid in an amount of about 20% by weight or greater; and a hydrophilic long-chain polymer, wherein at least a portion of the hydrophilic long-chain polymer comprises low methoxyl pectin.

In another aspect, the disclosure provides a method for preparing a gummy dosage form, comprising: providing a hydrocolloid system combining one or more hydrophilic bulking agents, one or more hydrophilic long-chain polymers, and one or more hydrating materials (e.g., water), wherein at least a portion of the hydrophilic long-chain polymer comprises low methoxyl pectin to give a mixture and heating the mixture to give a hydrocolloid system in the form of a slurry with a brix level of at least about 50%; combining an amino acid with the hydrocolloid system to give a substantially homogeneous amino acid-containing slurry comprising about 20% or more amino acid by dry weight; and setting the amino acid-containing slurry to give the gummy dosage form. Such a method can, in some embodiments, comprise heating the slurry to an even higher brix level. In some embodiments, the method further comprises depositing the amino acid-containing slurry into a mold prior to the setting step. The setting step can, in some embodiments, require addition of one or more ions or ion sources (at any stage of the method of preparing), e.g., one or more calcium ions or calcium ion sources, to effectively set the slurry and achieve the desired gummy dosage form. As such, in certain embodiment, the method can further comprise incorporating one or more such ions or ion sources during the providing or combining step.

The content of low methoxyl pectin in the disclosed gummy dosage forms can vary and, in some embodiments, at least about 50%, at least about 75%, at least about 90%, or substantially all of the hydrophilic long-chain polymer comprises low methoxyl pectin. In some embodiments, the amino acid is a monomeric amino acid. For example, the amino acid can comprise serine, including, but not limited to, L-serine. The amount of amino acid present in the gummy dosage form is advantageously high and, in certain embodiments, the amount of amino acid present is about 30% by weight or greater or about 35% by weight or greater, including about 30% to about 50% by weight, 35% to about 50% by weight, or about 35% to about 45% by weight.

The hydrophilic bulking agent in certain embodiments comprises one or more saccharides or saccharide derivatives, e.g., one or both of sugar solids and granulated sugars; and/or comprises one or more hydrogenated carbohydrates. Certain specific hydrophilic bulking agents used in various embodiments include, but are not limited to, glucose, sucrose, sorbitol, and/or fructose (e.g., a combination of sucrose and fructose). Various additional food-grade additives can be incorporated within the disclosed gummy dosage forms, including, but not limited to, additives selected from the group consisting of flavorants, colorants, fiber, and pH-adjusters. Exemplary pH adjusters include acids and buffers. In some embodiments, the gummy dosage form further comprises one or more ions or ion sources (e.g., one or more calcium ions or ion sources) responsible for "setting" the gummy form during production. In some embodiments, the gummy dosage form is substantially homogeneous. In other embodiments, the gummy dosage form includes one or more flavorants and/or colorants that are non-homogeneously associated with the gummy dosage form (e.g., in the form of a "swirl" or other pattern on the surface and/or within the gummy dosage form).

BRIEF DESCRIPTION OF THE FIGURES

FIG. 1 is a plot of data from an accelerated stability study of certain gummy dosage forms as disclosed herein, plotting amount of active ingredient remaining at various time points; and FIG. 2 is a plot of data from a high temperature stability study of certain gummy dosage forms as disclosed herein, plotting percent of active ingredient remaining at various time points.

DETAILED DESCRIPTION OF THE INVENTION

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a," "an," and "the" include plural referents unless the context clear dictates otherwise.

The disclosure relates to gummy dosage forms for oral use that are suitable particularly for the delivery of active ingredients, including amino acids in relatively high concentrations, in a manner that is highly palatable and that provides compliance with dosing requirements for the active ingredients. The disclosure also relates to methods of preparing such gummy dosage forms.

A "gummy" or "gummy dosage form" as used herein is understood to refer to a confectionary that can be defined by its compositional nature, as otherwise described herein, and also by its chewy texture and mouthfeel. Gummy bears, gummy worms, and other gummy candies are known in the art, and a person of ordinary skill in the art would understand the term "gummy" to refer to a composition having such texture and mouthfeel. It is noted that the gummy dosage forms disclosed herein may vary somewhat in texture and mouthfeel. For example, gummy dosage forms with lower amounts of amino acid included therein (e.g., around 20% by weight or less) are lightly chewy and smooth, while gummy dosage forms with higher amounts of amino acid included therein (e.g., around 40% by weight or more) are chewier and somewhat gritty in texture. All such textures and mouthfeels are intended to be included within the general definition of "gummy." Further information on gummy product components and properties is provided, for example, in U.S. patent application Ser. No. 15/092,283 to Romanoschi et al., filed Apr. 6, 2016 and U.S. patent application Ser. No. 15/092,332 to Romanoschi et al., filed Apr. 6, 2016, which are incorporated herein by reference in their entireties.

The "active ingredient" included within the gummy dosage forms disclosed herein can be any compound, composition, or like material that may be included in a dosage form for delivery to an individual to achieve any one or more of a desired nutritional purpose, medicinal purpose, and therapeutic purpose. The types and amounts of active ingredients incorporated within the disclosed gummy dosage forms include, but are not limited to, those active ingredients disclosed in U.S. patent application Ser. No. 15/092,283 to Romanoschi et al., filed Apr. 6, 2016 and U.S. patent application Ser. No. 15/092,332 to Romanoschi et al., filed Apr. 6, 2016, which are incorporated herein by reference in their entireties. In various embodiments disclosed herein, the active ingredient comprises at least one amino acid (e.g., a dietary amino acid). Amino acids are compounds containing carbon, hydrogen, oxygen, and nitrogen and various other elements can be found in the side chains of certain amino acids. About 500 amino acids are known and can be classified in various ways (including proteinogenic and non-proteinogenic amino acids). In certain embodiments, the active ingredient included within the gummy dosage forms disclosed herein comprises serine (and in particular, L-serine). Serine (2-amino-3-hydroxypropanoic acid) is a proteinogenic amino acid, which is found naturally (in its L-stereoisomeric form), in proteins. L-serine is synthesized within the human body under normal physiological circumstances from metabolites such as glycine, and is thus considered to be a "non-essential" amino acid, as it is not critical to the human diet. L-serine can be synthesized outside of the body, e.g., by fermentation starting from methyl acrylate.

The gummy dosage forms disclosed herein advantageously contain a high concentration of the one or more active ingredients (e.g., L-serine), e.g., at least about 20% by weight, at least about 30% by weight, or at least about 40% by weight. In some embodiments, the gummy dosage forms contain one or more active ingredients in an amount of about 20% to about 50% by weight or about 30% to about 50% by weight, e.g., about 35% to about 45% by weight. At certain high active ingredient contents, e.g., greater than about 50% amino acid by weight, some gummy formulations do not exhibit sufficient setting properties and/or do not exhibit sufficient physical properties (e.g., the desired "gummy" consistency). Such high concentrations are particularly advantageous for the delivery of certain active ingredients and with regard to certain disorders.

The gummy dosage forms disclosed herein can further comprise, in addition to the one or more active ingredients, one or more components, such as those components typically employed in gummy products, including, but not limited to, gellants, sweeteners, water, colorants, and flavorants. Gummy dosage forms generally comprise hydrocolloid systems, which can comprise, in some embodiments, one or more hydrophilic long-chain polymers, one or more hydrophilic bulking agents, and a hydrating material (water source). Optionally, the hydrocolloid system can include one or more further ingredients, such as pH modifiers, coloring agents, and/or flavoring agents. The gummy dosage form can further comprise one or more ions or ion sources, which can, in some embodiments, function to "set" the gummy form.

Hydrophilic, long-chain polymers useful in such hydrocolloid systems include, but are not limited to, long chain carbohydrates (e.g., polysaccharides) as well as various proteins. The hydrophilic, long-chain polymer preferably is configured to thicken and form a gel upon hydration (with or without heating). Non-limiting examples of hydrophilic, long-chain polymers that may be included in a hydrocolloid system for use within the gummy dosage forms disclosed herein include gelatin, pectin (including modified and unmodified forms of pectin), carrageenan, gellan gum, locust bean gum, gum arabic, xanthan gum, starch, methylcellulose, agar, konjac, alginates, and combinations thereof (including single, binary, tertiary, or quaternary blends). In certain embodiments, the amount of gelatin is limited, e.g., the hydrophilic, long-chain polymers of the disclosed gummy dosage forms comprise about 10% or less gelatin by weight, about 5% or less gelatin by weight, about 2% or less gelatin by weight, about 1% or less gelatin by weight, or substantially no gelatin by weight.

Certain hydrophilic bulking agents can include saccharides or saccharide derivatives. In various embodiments, hydrophilic bulking agents can include oligofructose, dextrins, monosaccharides (e.g., fructose or glucose), disaccharides (e.g., palatinose or sucrose), hydrogenated carbohydrates, also known as sugar alcohols (e.g., polyols, monosaccharide alcohols, disaccharide alcohols, or oligosaccharide alcohols, such as sorbitol), and syrups (e.g., glycose syrup or fructose syrup). The hydrophilic bulking agent may be a synthetic material, such as soluble fiber (e.g., polydextrose).

Advantageously, according to the present disclosure, the hydrocolloid system comprises pectin and, particularly, low-methoxyl pectin. Pectin is a heteropolysaccharide that is rich in galacturonic acid. Pectin is available in both high methoxyl and low methoxyl forms, wherein the reference to "methoxyl" refers to the number of carboxyl groups on the pectin backbone that are methyl esters. Typically, "low-methoxyl" pectin, described as being particularly desirable in the products and methods disclosed herein, is understood to comprise less than about 50% esterified carboxyl groups.

In certain preferred embodiments, the hydrophilic, long-chain polymer component of the products disclosed herein comprises about 25% or more by weight of pectin (e.g., low methoxyl pectin). More particularly, the pectin can comprise about 50% or more, about 75% or more, about 90% or more, substantially all, or all of the hydrophilic, long-chain polymer component of the hydrocolloid system. Low methoxyl pectin can be useful as it is more sugar and temperature dependent than, e.g., high methoxyl pectin (allowing for greater control over the gummy dosage form setting properties and allowing for a broader range of pH adjustment to achieve the desired properties in the final dosage form). Thus, as the setting properties of low methoxyl pectin are not dependent on pH (unlike various other hydrocolloids), the pH of the gummy dosage form can be adjusted as desired without significantly affecting the ability of the material to set. For example, low methoxyl pectin can be ion- or solid-setting types. Where the gummy dosage form comprises an ion-setting hydrophilic, long-chain polymer component, one or more ions or ion sources (e.g., $Ca^{2+}$) are generally incorporated within the gummy dosage form to achieve the desired setting of the material.

It is generally understood that, where calcium is used as a gelling agent, there are minimum levels of calcium needed to create a gel. Above that level, the gel strength of the composition increases rapidly until it reaches maximum saturation (after which point adding additional calcium will result in a decrease in the gel strength). In some embodiments, a sequestrant is used to control the availability of the calcium present in a given composition; as sequestrant levels increase, the system will gel less easily and at lower temperatures. Typically, as pH increases (i.e., as acidity decreases), pectin with a higher reactivity will be required to form a gel. Useful ion sources for gellation of certain compositions disclosed herein (e.g., those containing low methoxyl pectin) include all food-grade calcium-containing compounds and salts. Particular such calcium sources include, but are not limited to, calcium lactate, calcium gluconate, and calcium chloride. The amount of calcium source in the disclosed compositions can vary, e.g., from about 0.01 to about 15% by weight of the composition.

It is noted that the different types of low methoxyl pectin can lead to somewhat different textures of gummy dosage forms into which they are incorporated. Typically, however, gummy dosage forms as described herein which comprise the noted low methoxyl pectin content exhibit acceptable properties. For example, such gummy dosage forms generally set in a reasonable amount of time, e.g., within an hour and generally dry in a reasonable amount of time, e.g., within about 72 hours (e.g., in about 4-72 hours) if deposited in a mold (e.g., a starch tray) and exhibit acceptable textural properties). If deposited on a silicone mold, such forms generally require little to no drying time.

Where the hydrophilic, long-chain polymer component comprises less than all pectin (e.g., low methoxyl pectin), the remaining portion of the hydrophilic, long-chain polymer component can comprise any other type (or types) of hydrophilic, long-chain polymer known for use in such materials. Exemplary additional such components include, but are not limited to, any one or more of the types of hydrophilic, long-chain polymers referenced herein above. In certain specific embodiments, the hydrophilic, long-chain polymer component comprises a mixture of low methoxyl pectin and high methoxyl pectin or a mixture of low methoxyl pectin and carrageenan. In some embodiments, the hydrophilic, long-chain polymer component of the products disclosed herein comprises a significant percentage of gellan or a significant percentage of sodium alginate or gellan gum. For example, at least about 50% by weight, at least about 75% by weight, at least about 90% by weight, substantially all, or all of the hydrophilic, long-chain polymer component can comprise gellan or sodium alginate.

The hydrophilic bulking agent component in the hydrocolloid systems typically includes one or more saccharides or saccharide derivatives. In exemplary embodiments, hydrophilic bulking agents can include oligofructose, dextrins, monosaccharides (e.g., fructose or glucose), disaccharides (e.g., platinose or sucrose), hydrogenated carbohydrates, also known as sugar alcohols (e.g., polyols, monosaccharide alcohols, disaccharide alcohols, or oligosaccharide alcohols) and syrups (e.g., glucose syrup or fructose syrup). The hydrophilic bulking agent further may be a synthetic material, such as soluble fiber (e.g., polydextrose).

The hydrating material (water source) of the hydrocolloid systems can include any variety of materials configured to donate water to the hydrophilic, long-chain polymer. The hydrating material particularly can be substantially pure water; however, the hydrating material may be an aqueous composition including one or more additives, such as a syrup, a fruit juice, or a flavoring liquid.

In some embodiments, a pH modifier included in the hydrocolloid system particularly can be an acidifier. Non-limiting examples of acidic materials that can be used include citric acid, malic acid, lactic acid, tartaric acid, fumaric acid, phosphoric acid, ascorbic acid, sodium bisulfate, and combinations thereof. Flavoring agents can by natural or artificial and include, but are not limited to, citric acid, tartaric acid, artificial sweeteners (e.g., acesulfame potassium, aspartame, neotame, saccharine, and sucralose); salts (e.g., sodium chloride); plant extracts (e.g., vanilla, luo han guo); vegetable juice, pulp, and/or extracts; fruit juice, pulp, zest, and/or extracts (e.g., strawberry, raspberry, blackberry, blueberry); nuts; seeds; warm sensation materials; cool sensation materials; tingling sensation materials; and essential oils.

The relative amounts of the components used in the hydrocolloid system in the oral gummy dosage forms provided herein can vary. The following embodiments exemplify the relative amounts of components that may be used, with all percentages on a weight/weight basis (the weight of the specific component relative to the total weight of the hydrocolloid system). In some embodiments, the hydrocolloid system can comprise about 60% to about 95%, or about 65% to about 90% w/w of the hydrophilic bulking agents (particularly one or more saccharides or saccharide derivatives). Within the above ranges, the hydrophilic bulking agent can comprise: about 10% to about 70%, about 15% to about 65%, or about 20% to about 60% w/w of sugar syrup solids; about 10% to about 70%, about 15% to about 65%, or about 20% to about 60% w/w of granular sugar (or an alternative hydrophilic bulking agent); and/or about 1% to about 30%, about 5% to about 20%, or about 8% to about 18% w/w of one or more hydrogenated carbohydrates.

The hydrocolloid system can comprise about 1% to about 20%, about 1% to about 15%, or about 2% to about 7% w/w of one or more hydrophilic, long-chain polymers. The hydrocolloid system can comprise about 5% to about 40%, about 10% to about 30%, or about 20% to about 28% w/w of water. In a non-limiting example, the hydrocolloid system in the gummy dosage forms disclosed herein comprises about 1% to about 4% by weight pectin (e.g., low methoxyl pectin), 0% to about 3% by weight of further hydrophilic, long-chain polymers; about 10% to about 70% by weight sugar syrup solids (e.g., corn syrup solids); about 10% to about 70% by weight granular sugar (e.g., sucrose); and 0% to about 30% by weight of hydrogenated carbohydrates; about 0% to about 1.5% by weight pH modifier; and the balance water, with the weight being based on the total weight of the hydrocolloid system.

The gummy dosage forms provided according to the present disclosure thus generally comprise a significant amount of hydrocolloid system (e.g., about 30% to about 70% by weight); a significant amount of active ingredient, as described herein above; up to about 2%, up to about 1.5%, or up to about 1% w/w of a pH modifier (e.g., about 0.1% to about 1%, about 0.2% to about 0.8%, or about 0.3% to about 0.6% w/w of the pH modifier); and up to about 4%, up to about 2%, or up to about 1% of coloring agents and can comprise up to about 4%, up to about 2%, or up to about 1% of flavoring agents.

In a non-limiting example, a gummy dosage form is provided which comprises about 0.1% to about 4% by weight pectin (e.g., low methoxyl pectin), 0% to about 3% by weight of further hydrophilic, long-chain polymers; about 10% to about 50% by weight sugar syrup solids (e.g., corn syrup solids); about 10% to about 50% by weight granular sugar (e.g., sucrose); 0% to about 30% by weight of hydrogenated carbohydrates; about 0.1% to about 1.5% by weight pH modifier (e.g., citric acid); flavorants and colorants in a total amount of 0% to about 2%, and the balance water, with the weight being based on the total weight of the gummy dosage form.

In certain embodiments of the present disclosure, a gummy dosage form is provided wherein the active ingredients are substantially homogenously distributed throughout the dosage form. In particular, the active ingredient is, in some embodiments, substantially homogeneously distributed throughout the hydrocolloid system. The gummy dosage forms may comprise an outer coating or may be uncoated. The gummy dosage forms can be provided in various sizes, shapes, and total weight. Exemplary gummy dosage forms as disclosed herein can be provided with masses including, but not limited to, masses in the range of about 1 g to about 6 g, or about 2 g to about 5 g.

The gummy dosage forms can be generally homogeneous with respect to all components thereof or can include one or more components in a non-homogeneous association with remaining components. For example, a gummy dosage form may be provided wherein one or more components is only partially blended into the composition, e.g., so as to produce the effect of a visual "swirl" of colorant and/or flavorant on and/or within the composition. Such "swirls" and other patterned non-homogeneities of colorants, flavorants, and/or other components are intended to be encompassed by the present disclosure.

The gummy dosage forms provided herein generally can be characterized as being elastic or viscoelastic materials, and can be described as substantially chewable. A "chewable" dosage form, while capable of being swallowed whole, is configured specifically for chewing prior to swallowing. As such, a chewable dosage form is specifically distinguishable from a non-chewable dosage form, such as a vitamin tablet or capsule that is intended to be swallowed whole. In some embodiments, the term chewable can thus mean that the dosage form is intended to be retained in the mouth of the consumer for a period of time prior to swallowing, during which time the dosage form may undergo a change in structure that facilitates ease of swallowing. The chewable dosage form may thus be reduced to smaller pieces through mastication. In some embodiments, the chewable dosage form may be configured to at least partially dissolve within the mouth of the consumer. As such, the chewable dosage form may also be dissolvable and may thus be referred to as a "melt-away" form.

It is understood that the oral dosage forms of the present disclosure may be configured for undergoing changes under various mouth conditions. Discussion herein of "mouth conditions" can relate to one or more characteristics (in any combination) associated with the presence of an item in the mouth of an individual. For example, mouth conditions can include any combination of temperature, moisture, and pH typically found in the mouth of a human as well as the shear, compression, and other mechanical forces that may be applied by the teeth during chewing. Mouth conditions can particularly relate to being in contact with saliva. In some embodiments, mouth conditions can particularly mean contact with saliva at the temperature and pH typically present in the human mouth.

The disclosure also provides methods for preparing gummy dosage forms. Specifically, the disclosed methods involve steps of preparing a hydrocolloid system slurry, heating the hydrocolloid system slurry to thicken the slurry (and specifically to achieve a particular brix level) and subsequently adding the one or more active ingredients thereto to provide a gummy dosage form.

Generally, a slurry comprising the hydrocolloid system (including the hydrophilic long-chain polymer, hydrophilic bulking agent, water, and other optional components as disclosed herein above) is prepared. The components can be combined in various orders. For example, in one embodiment, at least a portion of the hydrophilic bulking agent is first mixed with the hydrophilic long-chain polymer and water is added thereto. This first mixture can be stirred and, optionally heated to allow for dissolution of the hydrophilic long-chain polymer. To this mixture, the remaining components, including the remainder of the hydrophilic bulking agent, are then added.

The slurry comprising the hydrocolloid system is heated to the desired concentration. Generally, the desired concentration can be defined by the brix level of the slurry, which can be monitored and measured as described herein below.

Brix is a unit of measurement of sugar content in an aqueous solution and 1 percent or 1 degree brix (Bx) is defined as 1 gram of sucrose in 100 grams of solution. Brix measurements are generally made by measuring the specific gravity of the solution/slurry using various instruments including, but not limited to, hydrometer, refractometer, pycnometer, or U-tube meter. The specific gravity can be converted to Bx, for example, using the Brix Table maintained by the National Institute of Standards and Technology. In some embodiments, the hydrocolloid slurry, just prior to addition of the active ingredient(s), has a Brix of at least about 50%, at least about 60%, at least about 70%, e.g., about 60-80% Brix or about 70-80% Brix.

The active ingredient(s) to be incorporated within a gummy dosage form are typically added to the slurry prior to heating (i.e., when the slurry is in less concentrated form) to ensure homogeneity of the resulting product. However, the inventors have found that the active ingredient(s) are advantageously added after heating the slurry to form a thickened slurry (i.e., when the slurry has achieved the brix levels referenced above). Incorporating the active ingredient at this stage is contrary to conventional practices, as one would not expect that mixing of the active ingredient with a concentrated slurry would be successful in providing a homogeneous mixture. The discovery that such an order of method steps surprisingly did provide the desired level of mixing arose from the observation by the inventors that certain active ingredients led to "browning" when incorporated within the slurry and heated in the conventional manner (believed to arise from Maillard reactions resulting from interaction between certain active ingredients and sugars present in the gummy dosage form). Surprisingly, they have found that adding the active ingredient(s) after the heating/cooking step (i.e., when the slurry has achieved the brix levels referenced herein above), a substantially homogenous mixture can still be obtained, with little to no noticeable browning during the process (as the composition containing the active ingredient is typically not subjected to further heating).

As such, according to the present disclosure, the slurry comprising the hydrocolloid system, which is subjected to mixing and heating, advantageously does not include the active ingredient(s). Rather, the hydrocolloid system is separately prepared and concentrated to provide a thickened slurry and at least a portion of the active ingredient to be included within the gummy dosage form is then added to the thickened slurry. Other components can be advantageously added post-heating as well, including, but not limited to, colorants, flavorants, and pH adjusters. In particular, where the hydrocolloid system comprises a hydrophilic long-chain polymer that sets at a certain pH, it may be advantageous to incorporate a pH adjuster to modify the pH of the composition to within the required range after the heating step (e.g., after addition of the active ingredient(s), preferably as the last component added).

The active ingredient-containing, thickened slurry is deposited into molds and cooled therein to set the final, desired shape when released from the molds to provide gummy dosage forms. The time required to achieve the gummy dosage forms after depositing into the molds can vary. Typically, sufficient setting of the slurry is achieved in the molds within an hour at ambient conditions (room temperature and ambient pressure) and sufficient drying of the slurry is achieved in the molds within about 72 hours, after which time the gummy dosage forms can be removed from the molds. It is noted that certain forms, e.g., those deposited on a silicone mold, require little to no drying time (e.g., less than about 1 hour). Advantageously, the gummy dosage forms exhibit sufficient integrity to remain in the desired form (without flowing) after removal from the molds. In some embodiments, the dosage forms removed from the molds can be processed, e.g., by applying oil or anti-sticking agents thereto, or by applying a coating as known in the art thereto.

In an alternative method for the preparation of gummy dosage forms and, particularly, for providing gummy dosage forms with reduced sugar content, a pan coating approach can be employed. In such methods, a sugar-based jelly bean center is provided and pan coated with a composition comprising the active ingredient(s), which can further comprise, e.g., flavorants (including sweeteners), colorants, pH modifiers, and the like. In some embodiments, the jelly bean center contains no active ingredient and, as such, only the coating of the dosage forms comprises the active ingredient. In other embodiments, the jelly bean center can contain active ingredient and additional active ingredient (which may be the same or different) can be included in the coating. In such embodiments, for example, the jelly bean center can comprise a hydrocolloid component comprising a hydrophilic long-chain polymer (e.g., low methoxyl pectin), prepared as disclosed herein above. The jelly bean center can comprise, e.g., about 20% or more by weight, about 30% or more by weight of the active ingredient, and the coating can similarly comprise, e.g., about 20% or more by weight or about 30% or more by weight of the active ingredient, such that a particularly high active ingredient loading is achieved (e.g., about 30% or more, about 40% or more, or about 50% or more by weight, based on the entire dosage form.

Gummy dosage forms as disclosed herein can provide a range of benefits. For example, serine serves a number of functions within the human body and the delivery of serine-containing dosage form as disclosed herein can provide such benefits in a concentrated, gummy dosage form (addressing concerns with compliant dosing in certain patient populations). For example, serine is understood to be an integral component of certain phospholipids that are important constituents of cellular membranes. Serine is also understood to make up brain protein and nerve coverings, to aid in the production of immunoglobulins and antibodies, and to be involved in the production of another amino acid (tryptophan), which is used in the production of serotonin. Dietary supplements comprising serine have been shown to be effective in treating chronic fatigue syndrome (which has been associated with serine deficiency). Serine has been found to be useful in the treatment of certain neurogenic disorders and various other serine deficiency-related disorders as well. For example, certain serine deficiency disorders include 3-phosphoglycerate dehydrogenase deficiency, 3-phosphoserine phosphatase deficiency, and phosphoserine aminotransferase deficiency. Such deficiency disorders can lead to severe neurological symptoms, which have been shown to be responsive to L-serine treatment. See, e.g., Tabatabaie, et al., "L-serine Synthesis in the Central Nervous System: A Review on Serine Deficiency Disorders," Mol. Genet. Metab. 2010 March; 99(3), 256-262, which is incorporated herein by reference in its entirety. Accordingly, the present disclosure provides for treatment of various conditions by administering the gummy dosage forms disclosed herein.

Embodiments of the present disclosure are further illustrated by the following examples, which are set forth to illustrate the presently disclosed subject matter and are not to be construed as limiting.

EXPERIMENTAL

Example 1: Gelling Agent Screen

A study was conducted to incorporate L-serine in various gummy formulations to evaluate the resulting products, as shown below in Table 1 to understand how L-serine affects gelling characteristics in different hydrocolloid systems. Standard formulations were employed, targeting 20% and 40% by weight L-serine and only the hydrocolloid system was modified between the samples. Briefly, samples were prepared by combining the referenced hydrophilic, long-chain polymer and sugar, adding water thereto, and heating until the resulting slurries reached a Brix level of 70-80. L-serine was then added to each slurry to target 20% and 40% L-serine-containing gummy dosage forms.

TABLE 1

Hydrocolloid System Variation

| Hydrophilic, long-chain polymer | General Observations |
|---|---|
| Pectin - high methoxyl | The high methoxyl pectin was a promising base for gummy dosage forms, as the dosage forms were produced and set well. Dosage forms comprising 20% L-serine loading and 33.3% L-serine loading were obtained. |
| Pectin - low methoxyl | The low methoxyl pectin was a promising base for gummy dosage forms, as the dosage forms were produced and set well. Dosage forms comprising 20% L-serine loading and 37.8% L-serine loading were obtained. |
| Pectin/Carrageenan | The pectin/carrageenan was a promising base for gummy dosage forms, as the dosage forms were produced and set well. Dosage forms comprising 38.6% L-serine loading were obtained. |
| Pectin/Carrageenan (half calcium) | The pectin/carrageenan (half calcium) was a promising base for gummy dosage forms, as the dosage forms were produced and set well. Dosage forms comprising 40.6% L-serine loading were obtained. |
| Sodium alginate base with calcium | The alginate samples did not behave as well as the pectin samples. The viscosity of the slurry became very high once L-serine was added and only a few pieces of gummies could reasonably be formed from the thickened slurry. After deposition, the gummy dosage forms did not appear to set sufficiently within the molds; a thin gel skin was formed in the samples, but the pieces were soft and sticky. Dosage forms comprising 20% L-serine loading and 28.6% L-serine loading were obtained. After storage for a day, the dosage forms exhibited "cold flow" and did not hold their shape (melted or stuck together to form a single mass). |
| Gellan gum | The gellan gum samples set quite well and could form gummy products. Dosage forms comprising 20% L-serine loading and 28.6% L-serine loading were obtained. |

Based on the observations provided above, it was determined that pectin (high and low methoxyl) and pectin/carrageenan were good candidates for the hydrophilic long-polymer component of the gummy dosage form hydrocolloid system. The low methoxyl pectin formulation was selected for further study due, in part to its sugar- and temperature-dependent setting properties.

Example 2: 20% L-Serine Gummy Dosage Form

A hydrocolloid slurry was formed including the ingredients below in Table 2. The slurry was formed by combining the water, sucrose, corn syrup, and pectin. This slurry was heated to achieve a target brix of 76% and a target pH of 4.4-4.6.

TABLE 2

Hydrocolloid System Slurry, 20% L-Serine Formulation

| Ingredient | Amount (g) |
|---|---|
| Water | 105.00 |
| Sugar (sucrose) | 156.97 |
| Corn syrup | 156.97 |
| Citrus pectin/sugar | 22.34 |

The slurry was combined with L-serine and citric acid in the amounts shown below in Table 3, targeting a 78% brix level and a pH of 3.4-3.6. The mixture was poured into molds and dried to give gummy dosage forms, each with a weight of 2.5 g. Sufficient gelling was observed to provide good dosage forms.

TABLE 3

Final mixture, 20% L-Serine Formulation

| Ingredient | Amount (g) |
|---|---|
| Hydrocolloid System Slurry (Table 2) | 240.00 |
| L-Serine | 60.00 |
| Citric acid | 10.00 |

Example 3: Stability Studies

Gummy dosage forms consistent with the formulations provided in Example 2 were evaluated for storage stability to gauge expected L-serine degradation of the shelf-life of such a product (a 6 month accelerated stability study).

Samples were stored in environmental chambers with active monitoring of L-serine content over time and maintained at various temperatures (25° C., 30° C., 40° C.). The data, presented as FIG. 1, indicates that, at conditions closer to room temperature (25° C. and 30° C.), there is no significant decline in L-serine over the testing time period. By contrast, at 40° C., there is a more pronounced decay in L-serine levels over time. This data not only shows that the dosage forms exhibit reasonable shelf stability, but also indicates that they are substantially uniform/homogenous, as results for multiple gummy dosage forms are comparable.

FIG. 2 provides high temperature stability data in terms of percentage of initial L-serine content remaining over time. The products maintained at milder conditions (25° C. and 30° C.) demonstrate little variation in the initial 100% content of L-serine. By contrast, the products maintained at 40° C. exhibit a concentration decrease in L-serine over time.

Example 4: 40% L-Serine Gummy Dosage Form

Low methoxyl pectin and sugar (sucrose) were mixed in the amounts in the first entry of Table 4 below, to provide a low-methoxyl pectin/sugar mixture and this mixture was combined with water and heated to boiling. The resulting slurry was heated for 2-3 minutes until the pectin was solubilized. The remaining components in Table 4 were added to the slurry and heating was continued until a brix of 71% was reached.

TABLE 4

Hydrocolloid System Slurry, for 40% L-Serine Formulation

| Ingredient | Amount (g) |
| --- | --- |
| Low-methoxyl pectin/sugar mixture | 56.3 (22.5 g pectin/33.8 g sugar) |
| Sugar (sucrose) | 294.0 |
| Corn syrup 43DE | 328.1 |
| Water | 219.0 |
| Dicalcium phosphate dihydrate | 2.7 |

A portion of the hydrocolloid system slurry was combined with L-serine in the amounts below in Table 5 and the slurry was mixed until the L-serine appeared dissolved. The remaining components in Table 5 were subsequently added, with phosphoric acid being added last, the mixture was stirred well, and deposited in starch molds (to provide pieces approximately 2.5 g each). The pieces were oiled with a small amount of glazing and anti-sticking product (e.g., Capol 410C). Again, sufficient gelling was observed to provide good dosage forms

TABLE 5

Final mixture, for 40% L-Serine Formulation

| Ingredient | Amount (g) |
| --- | --- |
| Hydrocolloid System Slurry (Table 4) | 461.20 |
| L-serine | 320 |
| Citric acid solution (50% in water) | 8.00 |
| Phosphoric acid | 8.00 |
| Stevia solution (2%) | 50 (1 g stevia/49 g water) |
| Flavor | 0.48 |
| Color solution | 0.32 |

The invention claimed is:

1. A gummy dosage form comprising:
   one or more hydrophilic bulking agents;
   one or more hydrating materials;
   an amino acid in an amount of about 20% by weight or greater; and
   a hydrophilic long-chain polymer, wherein at least a portion of the hydrophilic long-chain polymer comprises low-methoxyl pectin, and
   wherein the amino acid is a monomeric amino acid, comprising L-serine.

2. The gummy dosage form of claim 1, wherein at least about 50% of the hydrophilic long-chain polymer comprises low methoxyl pectin.

3. The gummy dosage form of claim 1, wherein substantially all of the hydrophilic long-chain polymer comprises low methoxyl pectin.

4. The gummy dosage form of claim 1, wherein the amino acid is present in an amount of about 30% by weight or greater.

5. The gummy dosage form of claim 1, wherein the amino acid is present in an amount of about 35% to about 50% by weight.

6. The gummy dosage form of claim 1, wherein the hydrophilic bulking agent comprises sucrose, fructose, or both sucrose and fructose.

7. The gummy dosage form of claim 1, further comprising one or more food-grade additives selected from the group consisting of flavorants, colorants, fiber, and pH-adjusters.

8. The gummy dosage form of claim 7, wherein the pH adjusters are selected from the group consisting of acids and buffers.

9. The gummy dosage form of claim 7, wherein the one or more of flavorants and colorants are non-homogeneously associated with the gummy dosage form.

10. The gummy dosage form of claim 1, wherein the dosage form is substantially homogeneous.

11. The gummy dosage form of claim 1, further comprising one or more calcium ions or ion sources.

12. A method for preparing the gummy dosage form of claim 1, comprising:
   providing a hydrocolloid system combining one or more hydrophilic bulking agents, one or more hydrophilic long-chain polymers, and one or more hydrating materials, wherein at least a portion of the hydrophilic long-chain polymer comprises low methoxyl pectin to give a mixture and heating the mixture to give a hydrocolloid system in the form of a slurry with a brix level of at least about 50%;
   combining an amino acid with the hydrocolloid system to give a substantially homogeneous amino acid-containing slurry comprising about 20% or more amino acid by dry weight; and
   setting the amino acid-containing slurry to give the gummy dosage form,
   wherein the amino acid is a monomeric amino acid, comprising L-serine.

13. The method of claim 12, wherein the providing or combining step further comprises incorporating one or more ions or ion sources.

14. The method of claim 12, wherein at least about 50% of the hydrophilic long-chain polymer comprises low methoxyl pectin.

15. The method of claim 12, wherein substantially all of the hydrophilic long-chain polymer comprises low methoxyl pectin.

16. The method of claim 12, wherein the amino acid-containing slurry comprises about 30% or more amino acid by dry weight.

17. The method of claim 12, wherein the amino acid-containing slurry comprises about 35% to about 50% amino acid by dry weight.

18. The method of claim 12, wherein the heating step comprises heating the slurry to a brix level of about 70% or greater.

19. The method of claim 12, further comprising depositing the amino acid-containing slurry into a mold prior to the setting step.

\* \* \* \* \*